(12) United States Patent
Tanida et al.

(10) Patent No.: US 6,214,378 B1
(45) Date of Patent: Apr. 10, 2001

(54) CAPSULES FOR ORAL PREPARATIONS AND CAPSULE PREPARATIONS FOR ORAL ADMINISTRATION

(75) Inventors: Norifumi Tanida; Jun Aoki; Masaru Nakanishi, all of Ibaraki (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/230,844

(22) PCT Filed: Aug. 1, 1997

(86) PCT No.: PCT/JP97/02686

§ 371 Date: Mar. 8, 1999

§ 102(e) Date: Mar. 8, 1999

(87) PCT Pub. No.: WO98/05310

PCT Pub. Date: Feb. 12, 1998

(30) Foreign Application Priority Data

Aug. 2, 1996 (JP) .................................. 8-205027

(51) Int. Cl.⁷ ............................................. A61K 9/48
(52) U.S. Cl. ........................................ 424/463; 424/451
(58) Field of Search ................................ 424/463, 451

(56) References Cited

U.S. PATENT DOCUMENTS 5,238,686 * 8/1993 Eichel et al. ........................ 424/461
5,462,951 * 10/1995 Iwao et al. .......................... 514/334
5,840,332 * 11/1998 Lerner et al. ....................... 424/464

* cited by examiner

Primary Examiner—Thurman K. Page
Assistant Examiner—Amy E Pulliam
(74) Attorney, Agent, or Firm—Wenderoth, Lind & Ponack, L.L.P.

(57) ABSTRACT

This invention offers capsules for oral preparation which is useful for colon diseases such as colon cancer, ulcerative colitis, constipation and diarrhea and for systemic diseases such as osteoporosis and which does not undergo any change at all in stomach and in small intestine but firstly start to disintegrate upon arriving at large intestine and, at the same time, quickly release the drug therefrom wherein the capsule base therefor is hydroxypropylmethylcellulose (HPMC) or polyethyleneglycol-compounded HPMC, gelatin or agar and, on the surface of said capsule base in which powder or liquid containing a pharmacologically active substance is encapsulated, a double-coated structure comprising an inner layer consisting of a cationic copolymer and an outer layer consisting of anionic copolymer is formed.

24 Claims, 8 Drawing Sheets

Behavior in gastrointestinal tracts of beagles after administration of barium sulfate capsules coated with a cationic copolymer ○ : not disintegrated yet    × : disintegrated △ : during disintegration

Fig. 2

| time | 2.5hr | 4hr | 5hr | 6hr | 7hr | 8hr | 9hr |
|---|---|---|---|---|---|---|---|
| stomach | ○○○○○ | | | | | | |
| small intenstine | ○○○○○<br>○○○○○<br>○○○○○ | ○○○○○ | | | | | |
| ascending colon | | ○ | ○○○ | | | | |
| transverse colon | | ○○○○○ | ○○○○ | ○△×× | | | |
| descending colon | | ○○○○○<br>○○○○ | ○○○○○<br>○○○○○<br>△×× | ○○○○○<br>○○○○○<br>△△△× | ○○○○△<br>△△△△△<br>×××× | ○○△△×<br>××××× | ○○△× |

Behavior in gastrointestinal tracts of beagles after administration of barium sulfate capsules (double-coated) and tablets ○ : not disintegrated yet     × : disintegrated △ : during disintegration

Fig. 3

| time | 2hr | 4hr | 5hr | 6hr | 7hr | 8hr |
|---|---|---|---|---|---|---|
| stomach | ○○○○○<br>○○○○○ | | | | | |
| small intenstine | ○○○○○<br>○○○○○ | ○○○○○<br>○○△△△ | △△△××<br>××× | ××× | | |
| ascending colon | | ○ | ○○○ | | | |
| transverse colon | | ○○○○○ | ○○○○ | ○△×× | | |
| descending colon | | ○△△△ | ○○△×× | △△△△△<br>× | △△×××<br>×× | ×× |

○ : not disintegrated yet     × : disintegrated

△ : during disintegration

Fig. 4

| time | 2hr | 3hr | 4hr | 5hr | 6hr | 7hr | 8hr | 9hr |
|---|---|---|---|---|---|---|---|---|
| stomach | OOOO OOOO OO | OOOO OOOO OO | OOOO O | OOOO O | | | | |
| small intenstine | OOOO OO | O | OOOO O | OOOO | OOOO OO | | | |
| ascending colon | O | OOO | O | O | | OOOO OO | OOO | |
| transverse colon | | OO | OOOO O | | | | OO | XXXX |
| descending colon | OOO | XXXX | | ΔΔΔΔ ΔΔ | ΔΔΔΔ ΔΔOO OO | ΔXXX XXXX XX | XX | X |

O : not disintegrated yet    X : disintegrated
Δ : during disintegration

Fig. 5

| time | 2.5hr | 4hr | 5hr | 6hr | 7hr | 8hr | 9hr | 10hr |
|---|---|---|---|---|---|---|---|---|
| stomach | ○○○○<br>○ | | | | | | | |
| small intenstine | ○○○○<br>○○○○<br>○○○○<br>○○○ | ○○○○<br>○ | | | | | | |
| ascending colon | | ○ | ○○○ | | | | | |
| transverse colon | | ○○○○<br>○ | ○○○○ | ○△×× | | | | |
| descending colon | | ○○○○<br>○○○○<br>○ | ○○○○<br>○○○○<br>○○△×<br>× | ○○○○<br>○○○○<br>○○△△<br>△× | ○○○○<br>△△△△<br>△△××<br>××× | ○○△△<br>××××<br>×× | ○○△× | ××× |

○ : not disintegrated yet     × : disintegrated

△ : during disintegration

Fig. 6

| time | 2.5hr | 4hr | 6hr | 8hr | 10hr | 12hr |
|---|---|---|---|---|---|---|
| stomach | OOOO | | | | | |
| small intenstine | OOOOO<br>OOOOO<br>OOOOO | OOO | | | | |
| ascending colon | O | OOOO | O | | | |
| transverse colon | | OOOOO<br>OOOOO<br>OOO | OOOO | O | | |
| descending colon | | | OOOOO<br>OΔΔΔΔ<br>ΔΔΔΔΔ | OOOΔΔ<br>ΔΔΔΔΔ<br>ΔΔΔΔΔ<br>XXXX | ΔΔΔΔX<br>XXXXX<br>XXXXX<br>X | XXXX |

O : not disintegrated yet    X : disintegrated

Δ : during disintegration

Fig. 7

| time | 2.5hr | 4hr | 6hr | 8hr | 10hr | 12hr | 14hr |
|---|---|---|---|---|---|---|---|
| stomach | OOOOO | | | | | | |
| small intenstine | OOOOO OOOOO OOOOO | OOOOO O | | | | | |
| ascending colon | | | | | | | |
| transverse colon | | OOOOO OOOOO OOOO | OOOOO | OO | | | |
| descending colon | | | OOOOO OOOOO OOOΔΔ | OOOOO OOOOO OOΔΔΔ ΔΔΔ | OOOOO OOOOO ΔΔΔΔΔ XXXXX | OOOXX XXX | |
| excrement in feces | | | | | | OOOOO OO | OOO |

O : not disintegrated yet    X : disintegrated

Δ : during disintegration eluting rate of prednisolone from capsules or tablets

CAPSULES FOR ORAL PREPARATIONS AND CAPSULE PREPARATIONS FOR ORAL ADMINISTRATION

FIELD OF THE INVENTION

1. Background of the Invention

This invention relates to capsules for preparations for oral administration and also to capsule preparations for oral administration using said capsules. More particularly, this invention relates to capsules being able to be administered orally in which pharmacologically active substance depending upon the object can be encapsulated and which is firstly disintegrated upon arriving at the large intestine whereby the pharmacologically active substance can be efficiently released therefrom and also relates to capsule preparations using said capsules where said preparations are pharmaceutical preparations useful for colon diseases such as colon cancer, ulcerative colitis, constipation and diarrhea and for systemic diseases such as osteoporosis.

2. Description of Related Art

In recent years, great effort has been made for developing the intestinal delivery art where the preparation after oral administration is not disintegrated in stomach and small intestine but is disintegrated just upon arriving at the large intestine. The reason is that such a method in place of conventional intravenous administration, transnasal administration, rectal administration, etc. greatly reduces the burden of the patients as compared with those conventional methods.

Examples of the known intestinal delivery art which have been known up to now are an oral preparation where a polymer which is soluble only at pH 5.5 or higher and an insoluble polymer are combined whereby large intestine is a target for releasing the drug (European Patent 49,590); a solid oral dosage form coated with an appropriate amount of anionic polymer (trade name: Eudragit S; manufactured by Rohm) which is soluble at pH 7.0 or higher (International Laid-Open Patent WO 83/00435); an oral preparation coated with a composition in an appropriate ratio of anionic copolymer which is soluble at pH 7.0 or higher (trade name: Eudragit S or L; manufactured by Rohm) and a methacrylate copolymer which is hardly soluble in water (trade name: Eudragit RS; manufactured by Rohm) (European Patent 225,189); an osmotic pressure pump preparation which is coated with an enteric coating polymer (Belgian Patent 903,502); and an oral pharmaceutical preparation delivering to large intestine where an internal layer which is soluble at pH 7.0 or higher is coated with a gelled polymer layer as an intermediate layer and then further coated with a stomach-resisting external layer which is soluble at pH 5.5 or higher (Japanese Laid-Open Patent Hei-04/501,411).

However, each of those known art relates to a preparation showing the time-depending release of drugs and their specificity to large intestine is high, cannot be said to be high. Thus, there are problems that, for example, when the staying time in small intestine is long, the preparation is disintegrated in the small intestine while, when the staying time in small and large intestines is short, the preparation is not disintegrated but is excreted outside as it is.

In order to improve such problems, the inventors of this invention proposed an oral pharmaceutical preparation of a type of releasing from lower gastrointestinal tracts having a high specificity to large intestine (International Laid-Open Patent WO 94/10983). This product is characterized in that it is a solid preparation having a double-coated structure where molded tablets or granules with pressure are used as cores and they are coated with an inner layer consisting of a cationic copolymer and an outer layer consisting of an anionic copolymer. This preparation has a very good specificity to large intestine and makes it possible to release the drug to the large intestine as a target in a more reliable manner. However, in spite of such an improvement, satisfactory releasing and absorbing efficiencies are not always achieved in the case of hardly-soluble substances and polymers. Therefore, it has been a very important matter to conduct a drug design depending upon the physical and chemical properties of the drug so that absorbing efficiency of the drug is further improved.

SUMMARY OF THE INVENTION

As a solution for the above-mentioned problems, this invention offers capsules for oral preparations, characterized in that, surface of the capsule base consisting of hydroxypropylmethylcellulose, a mixture of polyethylene glycol with hydroxypropylmethylcellulose, gelatin or agar is successively coated with a cationic copolymer and an anionic copolymer and also offers capsule preparations for oral administration where a pharmacologically active substance is encapsulated in said capsules.

BRIEF DESCRIPTION OF THE DRAWINGS

FIG. 2 is a drawing which shows that a double-coated capsule preparation is disintegrated in large intestine.

FIG. 3 is a drawing which shows the disintegrating state of a capsule #5 where each of the coating amounts of the inner and the outer layers is made 10 mg.

FIG. 4 is a drawing which shows the disintegrating state of a capsule #5 where each of the coating amounts of the inner and the outer layers is made 15 mg.

FIG. 5 is a drawing which shows the disintegrating state of a capsule #5 where each of the coating amounts of the inner and the outer layers is made 20 mg.

FIG. 6 is a drawing which shows the disintegrating state of a capsule #5 where each of the coating amounts of the inner and the outer layers is made 25 mg.

FIG. 7 is a drawing which shows the disintegrating state of a capsule #5 where each of the coating amounts of the inner and the outer layers is made 30 mg.

DESCRIPTION OF THE PREFERRED EMBODIMENTS

Figure 1:
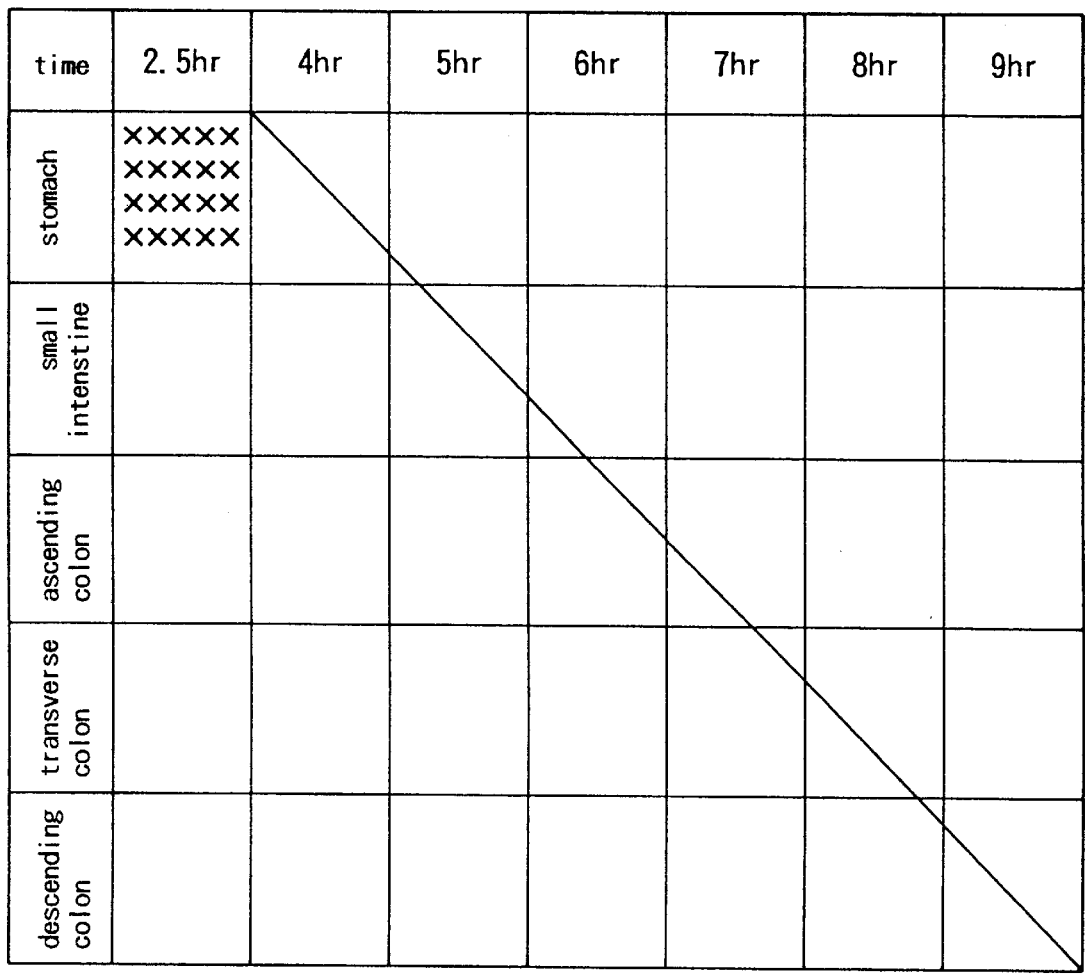
FIG. 1 is a drawing which shows that a capsule preparation which is coated with a cationic copolymer only is disintegrated in stomach.

This invention relates to the capsules as mentioned above and also to capsule preparations using the same where the capsule in which a pharmacologically active substance either in a form of liquid or powder is encapsulated is characterized in that said capsule has a specific base composition and also has a double-coated structure where the surface of the base has a cationic copolymer as an inner layer and an anionic copolymer as an outer layer. Here, the base for the capsule is hydroxypropylmethylcellulose, a mixture of polyethylene glycol with hydroxypropylmethylcellulose, gelatin or agar. Representative examples of the cationic copolymer which constitutes the inner layer of the double-coated layers are copolymer of methyl methacrylate with butyl methacrylate and dimethylaminoethyl methacrylate and polyvinylacetal diethylaminoacetate (AEA) (such as Eudragit E; manufactured by Roehm). Examples of viscosity of those cationic copolymer are around 1–30 centistokes (10 g; 100 ml methanol). Examples of the anionic copolymer which constitutes the outer layer are a copolymer of methacrylic acid with methyl methacrylate (such as Eudragit S; manufactured by Roehm), hydroxypropylmethylcellulose phthalate, hydroxypropylmethylcellulose acetate succinate, carboxymethylethylcellulose and cellulose acetate phthalate. Examples of viscosity of those anionic copolymers are around 5–60 centistokes (10 g; 100 ml methanol).

There is no particular limitation for the pharmacologically active substance to be encapsulated in the capsules so far as it is a substance which is effective when released in the lower gastrointestinal tracts and any of such substances may be used.

Thus, its examples are polypeptides, anti-inflammatory agents, anti-tumor agents, antibiotics, chemotherapeutic agents, remedies for ulcerative colitis, remedies for irritable colon syndrome, steroidal preparations, vitamins, drugs for diarrhea (including those for constipation), anti-sense drugs and immunosuppressants. To be more specific, the examples are insulin, angiotensin, vasopressin, calcitonin, gastrin, somatostatin, desmopressin, LH-RH (luteinizing hormone-releasing hormone), glucagon, oxytocin, gastrin, somatomedin, secretin, EGF(epidermal growth factor), $\alpha$-hANP ($\alpha$-human atrial natriuretic peptide), enkephalin, endorphin, GM-CSF (granulocyte-macrophage colony stimulating factor), G-CSF (granulocyte colony stimulating factor), human growth hormone, t-PA (Tissue plasminogen activator), TNF (tumor necrosis factor), TCGF (T-cell growth factor), ACTH (adrenocorticogropic hormone), interleukins, interferon, EPO (erythropoietin), urokinase, neocarcinostatin, immunoglobulin, muramyl dipeptide, MSH (melanocyte stimulating hormone), neurotensin, bombesin, endothelin, VIP (vasoactive intestinal polypeptide), CCK-8 (cholecystokinin 8), PTH (parathyroid hormone), CGRP (calcitonin gene-related peptide), TRH (thyrotropin-releasing hormone), diclofenac sodium, loxoprofen sodium, tenoxicam, lornoxicam, meloxicam, piroxicam, celecoxib, nimesulide, indomethacin, bleomycin, fluorouracil, tegafur, tegafur uracil, cisplatin, doxorubicin, cefpiramide sodium, cefsulodin sodium, kanamycin, erythromycin, cefoperazone sodium, ceftizoxime sodium, ceftriaxone sodium, cefmetazole sodium, cefotaxime sodium, cefazolin sodium, gentamycin, ceftezole sodium, cefamandole sodium, streptomycin, penicillin, tetracycline, salazosulfapyridine, budesonide, betamethasone sodium phosphate, prednisolone, mesalazine, methylprednisolone, hydrocortisone, beclometasone, $\beta$-carotene, sodium ascorbate, tocopherol, bisacodyl, picosulfate sodium, senna extract and cyclosporin. Incidentally, it goes without saying that those pharamcologically active substances cover their usual medically-acceptable inorganic and organic basic salts as well.

Incidentally, with regard to an anti-inflammatory agent, a cyclooxygenase (COX)-2 inhibitor is preferred. In addition, the pharmacologically active substance to be encapsulated in the capsule as well as the composition consisting of that and the following various additives to be added thereto are to be usually in a neutral or alkaoline region of around pH 7 or, preferably, lower than that. If necessary, additives such as vehicle, liquid agent, absorbefacient and others for various purposes may be compounded in the capsule. The vehicle at that time is appropriately selected from lactose, starch, talc, lactose, calcium hydrogen phosphate, sodium hydrogen phosphate, synthetic aluminum silicate, megnesium meta-silicate aluminate, aluminum magensium hydroxide, synthetic hydrotalcite, magensium silicate, natural aluminum silicate, potassium, carbonate, calcium carbonate, sodium carbonate, magnesium oxide, magnesium carbonate, sodium hydrogen carbonate, potassium hydrogen carbonate, silicic acid anhydride, light silicic acid anhydride, sodium hydroxide, tetrasodium pyrophosphate, anhydrous sodium pyrophosphate, anhydrous trisodium phosphate, dipotassium phosphate, anhydrous sodium sulfite, sodium ditartrate, etc. Incidentally, in adjusting the pH of the pharmaceutical-containing composition in the capsules, the adjustment may be conducted by selecting from those vehicles if necessary.

In the case of a liquid preparation, the use of glycerol, soybean oil, polyethylene glycol 400 (PEG 400), docosahexaenoic acid, eicosapentaenoic acid, pirotiodecane (chemical name: 1-[2-(decylthio)ethyl]azacyclopentan-2-one), sesame oil, safflower oil, cotton seed oil and olive oil may be exemplified. Further, with an object of accelerating the absorption of the pharmacologically active substance, absorbefacient such as sucrose fatty acid ester, glycyrrhizinate, glycyrrhetinic acid, bile acid and conjugated compound thereof, pirotiodecane, glycerol fatty acid ester, adipic acid, basic amino acid, polyethylene glycol, sodium caprate, sodium dodecyl sulfate and sodium deoxycholate may be added.

An example of the method for the manufacture of the preparation is as follows. Liquid in which a pharmacologically active substance or powder containing it and various additives are dissolved or dispersed is filled in the above-mentioned base capsule. Then a cationic copolymer is coated on the surface of the capsule after filling and then an anionic copolymer is coated thereon. In conducting the coating, the core is, for example, previously heated at 30–50° C. and then a coating solution is continuously sprayed thereon at 30–50° C.

An increase in weight by coating the cationic copolymer and the anionic copolymer or, in other words, the coated amount is important as a practical and essential condition for the capsules for oral administration of the present invention. Said coating amount may vary depending upon the size of the capsule. Thus, the amount for inner layer (a cationic copolymer) and that for outer layer (an anionic copolymer) vary depending upon the size of the capsule and each of them is 5–200 mg, preferably 10–100 mg or, more preferably, 15–60 mg. To be more specific, the preferred amount is 35–60 mg, 30–50 mg, 25–35 mg, 20–30 mg or 15–25 mg each for the capsules of the sizes #1, #2, #3, #4 or #5, respectively. Optimum coating amount is around 45 mg, around 40 mg, around 30 mg or around 20 mg for the capsule of #1, #2, #3 or #5, respectively. Incidentally, the total coating amount of inner and outer layers is two-fold weight of the above-mentioned amount.

With regard to the coating amount for each of inner and outer layers, their ratio by weight may be from around 1:2 to around 2:1 but, usually, it is preferred to make it about in the same amount each.

Since there are capsules of various sizes, the above-mentioned weight range is regulated as 0.08–0.13 mg/mm$^2$ (the optimum amount being around 0.10 mg/mm$^2$) in terms of the coating amount to the surface area of the capsule. This corresponds to any of the sizes of from #1 to #5 of the capsule.

When the coating amount in each of inner and outer layers is outside of 5–200 mg or is outside of the above-exemplified ranges, it is difficult to achieve the capsules which are disintegrated in large intestine and also to achieve the capsule preparations using said capsules.

As a result of this preparation, disintegration is firstly initiated upon arriving at the large intestine and, at the same time, the pharmacologically active substance is quickly released. When a liquid preparation is filled in the inner part of the capsule, the pharamcologically active substance is efficiently dispersed even in the large intestine where water content is little. Accordingly, local concentration in the tissues of the large intestine smoothly increases whereby an excellent absorbing efficiency into blood is achieved.

The present invention will now be further illustrated by way of the following examples. It goes without saying, however, that this invention is not limited by those examples.

EXAMPLES

Example 1

<Manufacture of Capsules>

Hydroxypropylmethylcellulose (HPMC) capsules #3 (weight: about 50 mg; the same being used hereinafter as well) was coated with a solution having the following composition.

| Eudragit E | 7.0 parts by weight |
| Ethanol | 70.0 parts by weight |
| Water | 19.5 parts by weight |
| Talc | 3.5 parts by weight |

The actual operation was that the above solution of 50° C. was coated by means of a continuous spraying onto the core of the capsule base which was previously heated at 50° C. An increase in weight of the core was 30 mg. After spraying, the core was dried and a solution having the following composition of 50° C. was further coated by means of a continuous spraying onto the previously coated core which was previously heated at 50° C.

| Eudragit S | 7.0 parts by weight |
| Ethanol | 70.0 parts by weight |
| Water | 18.8 parts by weight |
| Talc | 3.5 parts by weight |
| Polyethylene glycol 6000 | 0.7 part by weight |

An increase in weight was 30 mg.

Example 2

<Manufacture of Double-Coated Barium Sulfate Capsules>

Powder containing barium sulfate in the following formulation was filled in an HPMC capsule #3 to prepare a capsule having a weight of 425 mg.

| Barium sulfate | 375 mg |

This capsule core was coated with a solution having the following composition.

| Eudragit E | 7.0 parts by weight |
| Ethanol | 70.0 parts by weight |
| Water | 19.5 parts by weight |
| Talc | 3.5 parts by weight |

Thus, a coating was conducted by a continuous spraying of the above solution of 50° C. onto the core which was previously heated at 50° C. An increase in the weight of the core as a result of the inner layer coating was 30 mg. After spraying, the coated core was dried, heated at 50° C. and coated with a continuous spraying of a solution having the following composition kept at 50° C.

| Eudragits | 7.0 parts by weight |
| Ethanol | 70.0 parts by weight |
| Water | 18.8 parts by weight |
| Talc | 3.5 parts by weight |
| Polyethylene glycol 6000 | 0.7 part by weight |

An increase in weight as a result of the outer layer coating was 30 mg.

<Manufacture of Barium Sulfate Capsules Coated with Cationic Copolymer>

Meanwhile, for comparison, powder containing barium sulfate in the following formulation was filled in an HPMC #3 capsule to manufacture a capsule having a weight of 425 mg.

| Barium sulfate | 375 mg |

Incidentally, this core was coated with a solution having the following composition.

| Eudragit E | 7.0 parts by weight |
| Ethanol | 70.0 parts by weight |
| Water | 19.5 parts by weight |
| Talc | 3.5 parts by weight |

The actual operation was that the above solution of 50° C. was coated by means of a continuous spraying onto the core which was previously heated at 50° C. An increase in weight of the core was 30 mg.

Test Example 1

<An in vivo Test of Barium Sulfate Capsules in Dogs>

Barium sulfate capsules manufactured in Example 2 were administered to dogs and X-ray pictures were taken periodically whereby the transfer and disintegration in gastrointestinal tracts were observed. The result was that, as shown in FIG. 1, barium sulfate capsules coated with a cationic copolymer (comparative example) were disintegrated in stomach while, as shown in FIG. 2, double-coated barium sulfate capsules (example of this invention) were disintegrated in large intestine.

Test Example 2

<Evaluation of Optimum Coating Amount by an in vivo Test in Dogs Using Barium Sulfate capsules>

Taking the Test Example 1 into consideration as well, an optimum coating amount to capsules was evaluated. A double coating by the same formulations as in Example 2 was conducted in different coating amounts (i.e., in different increase in weight) on capsules having different sizes (from 190 1 to 190 5). Incidentally, in all cases, coating amounts of inner layer (a cationic copolymer) and outer layer (an anionic copolymer) were made same.

Specific mode of the test and the result thereof are as follow.

Thus, at first, five kinds of barium capsules were prepared using capsules of #5. The coating amount for each of inner and outer layers was 10 mg for the lowest while it was 30 mg for the highest. Four beagles were used and each five capsules were orally administered to each animal and the behavior of the capsules after administration was observed by taking X-ray pictures.

A shown in Table 1, when capsules #5 were used, disintegration of the preparations in the case where coating amount in each of inner and outer layers was 15–25 mg was 100% in large intestine while, in the case of other coating amounts, there were a few preparations where disintegration was noted in small intestine (capsule number 5-1) or non-disintegrated preparation was excreted into feces (capsule number 5—5).

Incidentally, the term "fig. no" in Table 1 stands for FIG. 3 to FIG. 7 attached.

Similarly, capsules of #3 were used and preparations where coating amount in each of inner and outer layers was 20–40 mg were prepared. Then disintegration of the preparations by an in vivo test using the dogs was investigated whereupon, as shown in Table 2, a large intestine specificity of 100% was noted in the preparations when a coating amount was 25–35 mg. Further, in vivo disintegration tests were conducted using the dogs for capsules #2 (Table 3) or capsules # 1 (Table 4) whereupon 100% disintegration which was specific to large intestine was confirmed in the case where the coating amounts were 30–50 mg and 35–60 mg for each of inner and outer layers for the capsules #2 and capsules #1, respectively.

TABLE 1

Investigation on Optimum Coating Amount for # 5 Capsule Preparations

| Capsule No. | Fig No. | Coating Amount (mg) for Inner Layer (Cationic) of Capsules | Outer Layer (Anionic) of Capsules | Numbers of Caps Disintegrated in Small Intestine | Large Intestine | Numbers of Caps Excreted into Feces without Disintegration |
|---|---|---|---|---|---|---|
| 5-1 | 3 | 10 | 10 | 8 (40%) | 12 (60%) | 0 (0%) |
| 5-2 | 4 | 15 | 15 | 0 (0%) | 20 (100%) | 0 (0%) |
| 5-3 | 5 | 20 | 20 | 0 (0%) | 20 (100%) | 0 (0%) |
| 5-4 | 6 | 25 | 25 | 0 (0%) | 20 (100%) | 0 (0%) |
| 5-5 | 7 | 30 | 30 | 0 (0%) | 10 (50%) | 10 (50%) |

TABLE 2

Investigation on Optimum Coating Amount for # 3 Capsule Preparations

| Capsule No. | Coating Amount (mg) for Inner Layer (Cationic) of Capsules | Outer Layer (Anionic) of Capsules | Numbers of Caps Disintegrated in Small Intestine | Large Intestine | Numbers of Caps Excreted into Feces without Disintegration |
|---|---|---|---|---|---|
| 3-1 | 20 | 20 | 5 (25%) | 15 (75%) | 0 (0%) |
| 3-2 | 25 | 25 | 0 (0%) | 20 (100%) | 0 (0%) |
| 3-3 | 30 | 30 | 0 (0%) | 20 (100%) | 0 (0%) |
| 3-4 | 35 | 35 | 0 (0%) | 20 (100%) | 0 (0%) |
| 3-5 | 40 | 40 | 0 (0%) | 15 (75%) | 5 (25%) |

TABLE 3

Investigation on Optimum Coating Amount for # 2 Capsule Preparations

| Capsule No. | Coating Amount (mg) for Inner Layer (Cationic) of Capsules | Outer Layer (Anionic) of Capsules | Numbers of Caps Disintegrated in Small Intestine | Large Intestine | Numbers of Caps Excreted into Feces without Disintegration |
|---|---|---|---|---|---|
| 2-1 | 25 | 25 | 5 (25%) | 15 (75%) | 0 (0%) |
| 2-2 | 30 | 30 | 0 (0%) | 20 (100%) | 0 (0%) |
| 2-3 | 40 | 40 | 0 (0%) | 20 (100%) | 0 (0%) |
| 2-4 | 50 | 50 | 0 (0%) | 20 (100%) | 0 (0%) |
| 2-5 | 60 | 60 | 0 (0%) | 10 (50%) | 10 (50%) |

TABLE 4

Investigation on Optimum Coating Amount for # 1 Capsule Preparations

| Capsule No. | Coating Amount (mg) for Inner Layer (Cationic) of Capsules | Outer Layer (Anionic) of Capsules | Numbers of Caps Disintegrated in Small Intestine | Large Intestine | Numbers of Caps Excreted into Feces without Disintegration |
|---|---|---|---|---|---|
| 1-1 | 30 | 30 | 4 (20%) | 16 (80%) | 0 (0%) |
| 1-2 | 35 | 35 | 0 (0%) | 20 (100%) | 0 (0%) |
| 1-3 | 46 | 45 | 0 (0%) | 20 (100%) | 0 (0%) |
| 1-4 | 60 | 60 | 0 (0%) | 20 (100%) | 0 (0%) |
| 1-5 | 70 | 70 | 0 (0%) | 10 (75%) | 5 (25%) |

It is believed from the above results that, since disintegration in small intestine was noted when the coating amount for each of inner and outer layers was 10 mg in the case of capsule #5, it is not possible to arrive specifically to large intestine when the coating amount is less than that. In addition, since excretion of non-disintegrated preparations into feces was noted when the coating amount was 30 mg, there will be a possibility that, in the capsule #5, disintegration will not take place when the coating amount is more than that.

For the capsules in other sizes, it was evaluated from the result of the in vivo disintegration test that, when the coating amount for the capsule of each size is more than the range as shown in the following Table 5, an object of the preparation would not be achieved.

TABLE 5

| Capsule Size (#) | Outer Diameter (mm) | Length (mm) | Optimum Coating Amount (mg) | Minimum Coating Amount (mg) | Maximum Coating Amount (mg) |
|---|---|---|---|---|---|
| 1 | 6.9 | 20.9 | 45 | 35 | 60 |
| 2 | 6.35 | 19.3 | 40 | 30 | 50 |
| 3 | 5.82 | 17.3 | 30 | 25 | 35 |
| 5 | 4.89 | 12.4 | 20 | 15 | 25 |

Example 3

<Manufacture of Prednisolone Capsules (Liquid) and Tablets>

A liquid preparation containing prednisolone was manufactured according to the following formulation and filled in HPMC capsules #3 to prepare capsule preparations each weighing 150 mg.

| Prednisolone | 3.0 parts by weight |
|---|---|
| Sodium deoxycholate | 10.0 parts by weight |
| PEG 400 | 87.0 parts by weight |

For comparison, powder containing prednisolone was manufactured according to the following formulation and made into tablets of 7 mm diameter and 200 mg weight using a tablet-manufacturing machine.

| Prednisolone | 10.0 parts by weight |
|---|---|
| Lactose | 69.0 parts by weight |
| Crystalline cellulose | 10.0 parts by weight |
| Polyvinylpyrrolide (PVP) | 10.0 parts by weight |
| Magnesium stearate | 1.0 parts by weight |

Each of the cores was coated with a solution having the following composition.

| Eudragit E | 7.0 parts by weight |
|---|---|
| Ethanol | 70.0 parts by weight |
| Water | 19.5 parts by weight |
| Talc | 3.5 parts by weight |

An inner layer was prepared by a continuous spraying of the above-mentioned solution of 50° C. onto a core which was previously heated at 50° C. An increase in the core was 30 mg for a capsule and was 16 mg for a tablet. After spraying, the coated core was dried and was further sprayed with a solution having the following composition.

| Eudragit S | 7.0 parts by weight |
|---|---|
| Ethanol | 70.0 parts by weight |
| Water | 18.8 parts by weight |
| Talc | 3.5 parts by weight |
| Polyethylene glycol 6000 | 0.7 part by weight |

Thus, the above-mentioned solution of 50° C. was continuously sprayed onto a core which was previously heated at 50° C. An increase in the core as a result of coating the outer layer was 30 mg for a capsule and was 16 mg for a tablet.

Test Example 3

An in vivo Elution Test of Prednisolone Capsules (Liquid) and Tablets

Figure 8:
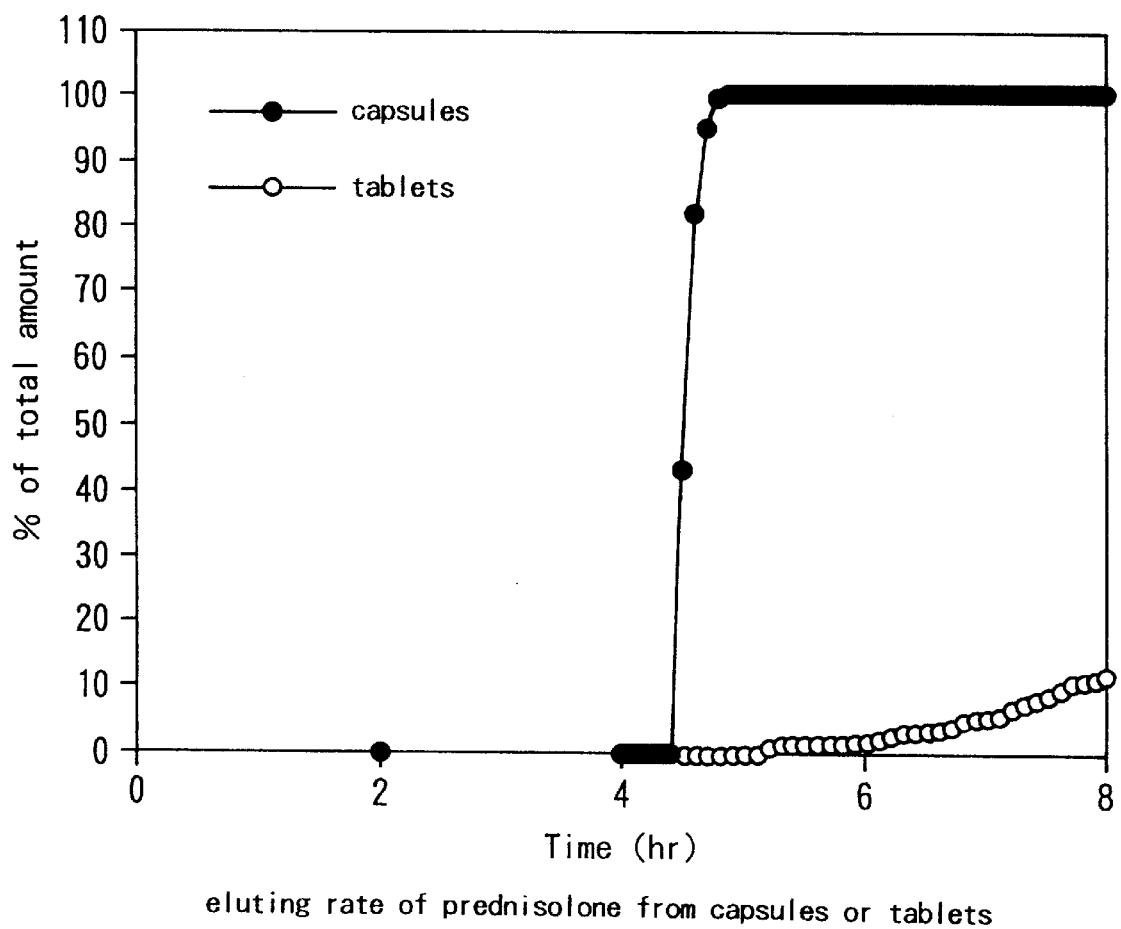
FIG. 8 is a drawing which shows dissolution of prednisolone from a capsule preparation of prednisolone (a liquid preparation) is quick as compared with the case of tablets.

Test of elution of prednisolone was conducted for prednisolone capsules and tablets manufactured in Example 3 by a flow-through-cell method (FTC). The result was that, as shown in FIG. 8, quick elution of the main ingredient was noted in capsules as compared with tablets.

Example 4

Manufacture of Calcitonin Capsules (Powder)

Powder containing calcitonin was manufactured according to the following formulation and filled in HPMC capsules #3 to manufacture capsules each weighing 150 mg.

| Calcitonin | 10.0 parts by weight |
|---|---|
| Sodium caprate | 45.0 parts by weight |
| Dipotassium glycyrrhizinate | 45.0 parts by weight |

The capsules were coated with a solution having the following composition.

| Eudragit E | 7.0 parts by weight |
|---|---|
| Ethanol | 70.0 parts by weight |
| Water | 19.5 parts by weight |
| Talc | 3.5 parts by weight |

Thus, coating was conducted by continuously spraying the above solution of 50° C. onto the core which was previously heated at 50° C. An increase in the core was 30 mg. After spraying, the coated core was dried, heated at 50° C. and a solution having the following composition was continuously sprayed to coat thereon.

| Eudragit S | 7.0 parts by weight |
|---|---|
| Ethanol | 70.0 parts by weight |
| Water | 18.8 parts by weight |
| Talc | 3.5 parts by weight |
| Polyethylene glycol 6000 | 0.7 part by weight |

An increase in weight was 30 mg.

Example 5

Manufacture of Calcitonin Capsules (Liquid)

Formulation 1

A liquid preparation containing calcitonin was manufactured according to the following formulation and filled in HPMC capsules #3 to give capsules each weighing 425 mg.

| Calcitonin | 10.0 parts by weight |
|---|---|
| Glycerol | 80.0 parts by weight |
| Sucrose fatty acid ester [F-160 (trade name); manufactured by Daiichi Kogyo Seiyaku K.K.] | 10.0 parts by weight |

Formulation 2

A liquid preparation containing calcitonin (CT) was manufactured according to the following formulation and filled in the same capsules as above to give capsules each weighing 425 mg.

| | |
|---|---|
| Calcitonin | 10.0 parts by weight |
| PEG 400 | 80.0 parts by weight |
| Sodium deoxycholate | 10.0 parts by weight |

After that, each of the capsules was coated with a solution having the following composition.

| | |
|---|---|
| Eudragit E | 7.0 parts by weight |
| Ethanol | 70.0 parts by weight |
| Water | 19.5 parts by weight |
| Talc | 3.5 parts by weight |

Thus, coating was conducted by continuously spraying the above-mentioned solution at 50° C. onto the core previously heated at 50° C. being coated with the inner layer already. An increase in weight by coating with the outer layer was 30 mg. After the spraying, the coated core was dried and further coated with a solution of the following composition.

| | |
|---|---|
| Eudragit S | 7.0 parts by weight |
| Ethanol | 70.0 parts by weight |
| Water | 18.8 parts by weight |
| Talc | 3.5 parts by weight |
| Polyethylene glycol 6000 | 0.7 part by weight |

Thus, coating was conducted by continuously spraying the above-mentioned solution of 50° C. onto the core which was previously heated at 50° C. coated with the inner layer. An increase in weight by coating with the outer layer was 30 mg.

Example 6
Manufacture of 5-Fluorouracil-Containing Capsules (Powder)

Powder containing 5-fluorouracil was manufactured according to the following formulation and filled in HPMC capsules #3 to give capsules each weighing 150 mg.

| | |
|---|---|
| 5-Fluorouracil | 50.0 parts by weight |
| Cross povidone | 50.0 parts by weight |

The resulting capsules were coated with a solution having the following composition.

| | |
|---|---|
| Eudragit E | 7.0 parts by weight |
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 30 mg. After the spraying, the coated core was dried and further coated with a solution of the following composition.

| | |
|---|---|
| Eudragit S | 7.0 parts by weight |
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 30 mg.

Example 7
Manufacture of 5-Fluorouracil Capsules (Liquid Preparation)

Formulation 1

A liquid preparation containing 5-fluorouracil was manufactured according to the following formulation and filled in HPMC capsules #3 to give capsules each weighing 300 mg.

| | |
|---|---|
| 5-Fluorouracil | 50.0 parts by weight |
| Soybean oil | 50.0 parts by weight |

Formulation 2

A liquid preparation containing 5-fluorouracil was manufactured according to the following formulation and filled in HPMC capsules #3 to give capsules each weighing 300 mg.

| | |
|---|---|
| 5-Fluorouracil | 50.0 parts by weight |
| PEG 400 | 50.0 parts by weight |

Each of the capsules was subjected to a coating having the following composition.

| | |
|---|---|
| Eudragit E | 7.0 parts by weight |
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 30 mg. After the spraying, the coated core was dried and further coated with a solution of the following composition.

| | |
|---|---|
| Eudragit S | 7.0 parts by weight |
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 30 mg.

Example 8

Manufacture of Capsules containing Sodium Betamethasone Phosphate (Powder)

Powder containing sodium betamethasone phosphate was manufactured according to the following formulation and filled in HPMC capsules #2 (weight: about 53 mg; and same being used hereinafter as well) to give capsules each weighing 200 mg.

| Sodium betamethasone phosphate | 4.0 parts by weight |
|---|---|
| Cross povidone | 50.0 parts by weight |
| Lactose | 46.0 parts by weight |

Each of the capsules was subjected to a coating having the following composition.

| Eudragit E | 7.0 parts by weight |
|---|---|
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 40 mg. After the spraying, the coated core was dried and further coated with a solution of the following composition.

| Eudragit S | 7.0 parts by weight |
|---|---|
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 40 mg.

Example 9

Manufacture of Sodium Betamethasone Phosphate (Liquid Preparation)

Formulation 1

A liquid preparation containing sodium betamethasone phosphate was manufactured according to the following formulation an filled in HPMC capsules #2 to give capsules each weighing 400 mg.

| Sodium betamethasone phosphate | 5.0 parts by weight |
|---|---|
| Soybean oil | 95.0 parts by weight |

Formulation 2

A liquid preparation containing sodium betamethasone phosphate was manufactured according to the following formulation and filled in HPMC capsules #2 to give capsules each weighing 400 mg.

| Sodium betamethasone phosphate | 5.0 parts by weight |
|---|---|
| PEG 400 | 95.0 parts by weight |

Each of the capsules was subjected to a coating having the following composition.

| Eudragit E | 7.0 parts by weight |
|---|---|
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 40 mg. After the spraying, the coated core was dried and further coated with a solution of the following composition.

| Eudragit S | 7.0 parts by weight |
|---|---|
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 40 mg.

Example 10

Manufacture of Budesonide (Liquid Preparation)

Formulation 1

A liquid preparation containing budesonide was manufactured according to the following formulation and filled in HPMC capsules #2 to give capsules each weighing 400 mg.

| Budesonide | 5.0 parts by weight |
|---|---|
| Soybean oil | 95.0 parts by weight |

Formulation 2

A liquid preparation containing budesonide was manufactured according to the following formulation and filled in HPMC capsules #2 to give capsules each weighing 400 mg.

| Budesonide | 5.0 parts by weight |
|---|---|
| PEG 400 | 95.0 parts by weight |

Each of the capsules was subjected to a coating having the following composition.

| Eudragit E | 7.0 parts by weight |
|---|---|
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 40 mg. After the spraying, the coated core was dried and further coated with a solution of the following composition.

| Eudragit S | 7.0 parts by weight |
| --- | --- |
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 40 mg.

Example 11
Manufacture of Diclofenac Sodium (Liquid Preparation)

A liquid preparation containing diclofenac sodium was manufactured according to the following formulation and filled in HPMC capsules #2 to give capsules each weighing 400 mg.

| Diclofenac sodium | 5.0 parts by weight |
| --- | --- |
| Glycerol | 95.0 parts by weight |

Each of the capsules was subjected to a coating having the following composition.

| Eudragit E | 7.0 parts by weight |
| --- | --- |
| Ethanol | 70.0 parts by weight |
| Water | 19.5 parts by weight |
| Talc | 3.5 parts by weight |

The inner layer was coated by continuously spraying the above-mentioned solution at 50° C. onto the core which was previously heated at 50° C. An increase in the core was 40 mg. After the spraying, the coated core was dried and further coated with a solution of the following composition.

| Eudragit S | 7.0 parts by weight |
| --- | --- |
| Ethanol | 70.0 parts by weight |
| Water | 18.8 parts by weight |
| Talc | 3.5 parts by weight |
| Polyethylene glycol 6000 | 0.7 part by weight |

The outermost layer was coated by continuously spraying the above-mentioned solution of 50° C. onto the core which was previously heated at 50° C. coated with the inner layer. An increase in weight by coating with the outer layer was 40 mg.

INDUSTRIAL APPLICABILITY offers a pharmaceutical preparation which does not undergo any change at all in stomach and in small intestine but firstly starts to disintegrate upon arriving at large intestine and, at the same time, quickly releases the drug therefrom. As a result thereof, it is now possible to offer a pharmaceutical preparation which is useful for colon diseases such as colon cancer, ulcerative colitis, constipation and diarrhea and for systemic diseases such as osteoporosis.

What is claimed is:

1. A capsule comprising a base layer consisting of hydroxypropylmethylcellulose, a mixture of polyethylene glycol with hydroxypropylmethylcellulose, gelatin or agar, the outside surface of said base layer being successively coated with an inner layer consisting of a cationic copolymer, and an outer layer consisting of an anionic copolymer.

2. The capsule according to claim 1, wherein the cationic copolymer is a copolymer of methyl methacrylate with butyl methacrylate and dimethylaminoethyl methacrylate or polyvinylacetal diethylaminoacetate.

3. The capsule according to claim 1, wherein the anionic copolymer is at least one selected from a group consisting of a copolymer of methacrylic acid with methyl methacrylate, hydroxypropylmethylcellulose phthalate, hydroxypropylmethylcellulose acetate succinate, carboxymethylethylcellulose and cellulose acetate phthalate.

4. The capsule according to any one of claims 1–3, wherein the cationic copolymer and the anionic copolymer is each in an amount of about 5 mg to about 200 mg.

5. The capsule according to claim 4, wherein the cationic copolymer and the anionic copolymer is each in an amount of about 15 mg to about 60 mg.

6. The capsule according to any one of claims 1–3, wherein the cationic copolymer and the anionic copolymer is each, in terms of weight to the surface area of the capsule, in a range of about 0.08–0.13 mg/mm$^2$.

7. A capsule preparation comprising the capsule according to any one of claims 1–3, and a pharmacologically active substance encapsulated in the capsule.

8. The capsule preparation according to claim 7, wherein the pharmacologically active substance is at least one selected from a group consisting of polypeptides, anti-inflammatory agents, anti-tumor agents, antibiotics, chemotherapeutic agents, remedies for ulcerative colitis, remedies for irritable colon syndrome, steroidal preparations, vitamins, drugs for constipation, anti-sense drugs and immunosuppressants.

9. The capsule preparation according to claim 7, wherein the pharmacologically active substance is contained in a liquid preparation, said liquid preparation being encapsulated in the capsule.

10. The capsule preparation according to claim 9, wherein the liquid preparation is at least one selected from the group consisting of glycerol, soybean oil, polyethylene glycol 400 (PEG 400), docosahexaenoic acid, eicosapentaenoic acid, pirotiodecane, sesame oil, safflower oil, cotton seed oil and olive oil.

11. The capsule preparation according to claim 9, further comprising an absorbefacient compounded with the liquid preparation.

12. The capsule preparation according to claim 11, wherein the absorbefacient is selected from a group consisting of sucrose fatty acid ester, glycyrrhizinate, glycyrrhetinic acid, bile acid and conjugated compound thereof, pirotiodecane, glycerol fatty acid ester, adipic acid, basic amino acid, polyethylene glycol, sodium caprate, sodium dodecyl sulfate and sodium deoxycholate.

13. The capsule preparation according to claim 7, which disintegrates in the lower gastrointestinal tracts and is for oral administration.

14. The capsule according to any one of claims 1–3, which disintegrates in the lower gastrointestinal tracts and is for oral administration.

15. A method of making a capsule comprising coating on the outside surface of a base layer of the capsule an inner layer consisting of a cationic copolymer, and further coating on said inner layer an outer layer consisting of an anionic copolymer.

16. The method according to claim 15, wherein the cationic copolymer is a copolymer of methyl methacrylate with butyl methacrylate and dimethylaminoethyl methacrylate or polyvinylacetal diethylaminoacetate.

17. The method according to claim 15, wherein the anionic copolymer is at least one selected from a group consisting of a copolymer of methacrylic acid with methyl methacrylate, hydroxypropylmethylcellulose phthalate, hydroxypropylmethylcellulose acetate succinate, carboxymethylethylcellulose and cellulose acetate phthalate.

18. The method according to any one of claims 15–17, wherein the cationic copolymer and the anionic copolymer is each coated in an amount of about 5 mg to about 200 mg.

19. A method of making a capsule preparation comprising encapsulating a pharmacologically active substance in a capsule obtained by the method according to any one of claims 15–17.

20. The method according to claim 19, wherein the pharmacologically active substance is at least one selected from a group consisting of polypeptides, anti-inflammatory agents, anti-tumor agents, antibiotics, chemotherapeutic agents, remedies for ulcerative colitis, remedies for irritable colon syndrome, steroidal preparations, vitamins, drugs for constipation, anti-sense drugs and immunosuppressants.

21. The method according to claim 20, wherein the pharmacologically active substance is dissolved or dispersed in a liquid preparation, and the liquid preparation is encapsulated in the capsule.

22. The method according to claim 21, wherein the liquid preparation is at least one selected from the group consisting of glycerol, soybean oil, polyethylene glycol 400 (PEG 400), docosahexaenoic acid, eicosapentaenoic acid, pirotiodecane, sesame oil, safflower oil, cotton seed oil and olive oil.

23. The method according to claim 21, further comprising an absorbefacient compounded with the liquid preparation.

24. The method according to claim 23, wherein the absorbefacient is selected from the group consisting of sucrose fatty acid ester, glycyrrhizinate, glycyrrhetinic acid, bile acid and conjugated compound thereof, pirotiodecane, glycerol fatty acid ester, adipic acid, basic amino acid, polyethylene glycol, sodium caprate, sodium dodecyl sulfate and sodium deoxycholate.

* * * * *